US006211200B1

(12) United States Patent
Luengo et al.

(10) Patent No.: US 6,211,200 B1
(45) Date of Patent: Apr. 3, 2001

(54) METAL COMPLEXES

(75) Inventors: Juan I. Luengo, Audubon, PA (US); Stephen G. Miller, San Diego, CA (US)

(73) Assignees: SmithKline Beecham Corporation, Philadelphia, PA (US); Ligand Pharmaceuticals, San Diego, CA (US)

( * ) Notice: Subject to any disclaimer, the term of this patent is extended or adjusted under 35 U.S.C. 154(b) by 0 days.

(21) Appl. No.: 09/183,935

(22) Filed: Oct. 30, 1998

Related U.S. Application Data

(60) Provisional application No. 60/065,409, filed on Oct. 31, 1997.

(51) Int. Cl.$^7$ .......................... A61K 31/44; A61K 31/415
(52) U.S. Cl. ......................... 514/333; 514/338; 514/388
(58) Field of Search ................................ 514/333, 338, 514/388

(56) References Cited

U.S. PATENT DOCUMENTS

| 5,693,515 | 12/1997 | Clark et al. | 435/184 |
|---|---|---|---|
| 5,767,078 | 6/1998 | Johnson et al. | 514/12 |
| 5,773,569 | 6/1998 | Wrighton et al. | 530/300 |
| 5,830,851 | 11/1998 | Wrighton et al. | 514/2 |
| 5,869,451 | 2/1999 | Dower et al. | 514/13 |
| 5,981,551 | * 11/1999 | Luengo et al. | 514/333 |

FOREIGN PATENT DOCUMENTS

WO99/11262   3/1999   (WO).

OTHER PUBLICATIONS

Botros et al., "Immobilized metal ion affinity partitioning of cells in aqueous two–phase systems:erythrocytes as a model", *Biochimica et Biophysica Acta*, 1074, pp. 69–73 (1991).

Arai et al., "Bleomycin Model Complex Bearing A Carbamoyl Derived Sustituent Capable of Coordination to the Chelated Metal Ion As A Sixth Ligand", *Bioorganic & Medicinal Chemistry Letters*, 7(1), pp. 15–18 (1997).

Rao et al., Technetium(V) and Rhenium(V) Complexes of 2,3–Bis(mercaptoacetamido)propanoate. Chelate Ring Stereochemistry and Influence on Chemical and Biologial Properties, *J. Am. Chem. Soc.*, 112, pp. 5798–5804 (1990).

Katz et al., "Design of potent selective zinc–mediated serine protease inhibitors", *Letters to Nature*, 391, pp. 608–613 (1998).

Bergeron et al., "Synthesis and Biological Evaluation of Naphthyldesferrithiocin Iron Chelators",*J. Med. Chem.,* 39, pp. 1575–1581 (1996).

Chi et al., "Homodimeric and Heterodimeric Bis(amino thiol) Oxometal Complexes with Rhenium(V) and Technetium(V). Control of Heterodimeric Complex Formation and an Approach to Metal Complexes that Mimic Steriod Hormones", *J. Med. Chem.*, 37, pp. 928–937 (1994).

Wrighton et al., "Small Peptides as Potent Mimetics of the Protein Hormone Erythropoietin", *Science*, 273, pp. 458–463 (1996).

Cwirla et al., "Peptide Agonist of the Thrombopoietin Receptor as Potent as the Natural Cytokine", *Science*, 276, pp. 1696–1699 (1997).

Linvah et al., "Functional Mimicry of a Protein Hormone by a Peptide Agonist:The EPO Receptor Complex at 2.8A", *Science*, 273, pp. 464–471 (1996).

Klekota et al., "Generation of Novel DNA–Binding Compounds by Selection and Amplification from Self–Assembled Combinatorial Libraries", *Tetrahedron Letters*, 38(50), pp. 8639–8642 (1997).

Chi et al., "Selective F ormation of Heterodimeric Bis–Bidentate Aminothiol–Oxometal Complexes of Rhenium(V)", *J. Am. Chem. Soc.*, 115, pp. 7045–7046 (1993).

Routier et al., "Salen–Anthraquinone Conjugates. Synthesis, DNA–Binding and Cleaving Properties, Effects on Topoisomerases and Ctotoxicity", *Bioorganic & Medicinal Chemistry*, 4(8), pp. 1185–1196 (1996).

* cited by examiner

Primary Examiner—Kevin E. Weddington
(74) Attorney, Agent, or Firm—Wayne L. Dustman; William T. King; Charles M. Kinzig

(57) ABSTRACT

Invented are zinc chelated G-CSF receptor ligands, pharmaceutical compositions containing these compounds, and methods of using these compounds as agonist of the G-CSF receptor. Also invented are novel processes used in preparing these compounds. Also invented are novel G-CSF receptor binding moieties of the invented zinc chelated G-CSF receptor ligands.

6 Claims, 5 Drawing Sheets

METAL COMPLEXES

This application claims the benefit of Provisional No. 60/065,409 filed Oct. 31, 1997.

FIELD OF THE INVENTION

This invention relates to G-CSFR metal complexed ligands, methods for making and identifying them and their use as agonist of G-CSFR.

BACKGROUND OF THE INVENTION

Granulocyte colony-stimulating factor (G-CSF) is a glycoprotein secreted by macrophages, fibroblasts, and endothelial cells originally identified by its ability to stimulate the survival, proliferation, and differentiation in vitro of predominantly neutrophilic granulocytes from bone marrow progenitors (Nicola, N. A., *Annu. Rev. Biochem.* (1989) 58:45). The capacity of G-CSF to regulate in vivo granulopoiesis is supported by animal and clinical studies, which demonstrated a reversible rise in circulating neutrophil levels in response to administered recombinant G-CSF (Gabrilove, J. L. et al., *N. Engl. J. Med.* (1988) 318:1414). G-CSF has pleiotropic effects on mature neutrophils, enhancing their survival and stimulating functional activation, including induction of neutrophil alkaline phosphatase (Sato. N. et al., *J. Cell. Physiol.* (1988) 37:272) and high affinity IgA $F_c$ receptors (Weisbart, R. H., et al., *Nature (Lond.)* (1988) 332:647), priming for respiratory burst (Nathan, C. F. *Blood* (1989) 73:301) and increased chemotaxis (Wang, J. M., *Blood* (1988) 72:1456). G-CSF effects have also been observed on hematopoietic cells that are not committed to the granulocyte lineage, for example, stimulation of the proliferation on monocytic differentiation in vitro of some myeloid leukemic cells (Geissler, K., *J. Immunol.* (1989) 143:140) and the proliferation in vitro of some multipotential hematopoietic precursors (Ferrero, D., *Blood* (1989) 73:402).

G-CSF activates intracellular processes by binding to the granulocyte colony stimulating factor receptor (G-CSF receptor) (Demetri, G. D. and Griffin J. D., Blood 1991, 78, 2791; Avalos, B. R. Blood, 1996, 88, 761). The G-CSF receptor is single transmembrane cytokine cell surface receptor composed of three domains: an extracellular ligand binding domain, a transmembrane domain, and an intracellular signal transduction domain. It is now clear that signal transduction by cytokines is accomplished by ligand-mediated receptor dimerization (Ullrich, A. and Schlessinger, J., "Signal transduction by receptors with tyrosine kinase activity", Cell, 61" 203–212 (1990); Kishimoto, T., Taga, T., and Akira, S., "Cytokine signal transduction", *Cell,* 76: 253–262 (1994); Heldin, C. H., "Dimerization of cell surface receptors in signal transduction", *Cell,* 80: 213–223 (1995); Lemmon, M. A. and Schlessinger, J., "Regulation of signal transduction and signal diversity by receptor oligomerization", *Trends Biol. Sci.,* 19: 459–463 (1994)). G-CSF binds to two receptor subunits resulting in homodimerization, an event that promotes activation of cytoplasmic tyrosine kinases that associate with the intracellular domain of the recptors. This tyrosine kinase activity then initiates a cascade of intracellular processes.

Administration of recombinant G-CSF to patients suffering from neutropenia due to various causes indicated that G-CSF is beneficial as an adjuvant in chemotherapy and in bone marrow transplantation (Morstyn, G., et al., *Trends Pharmacol. Sci.* 10, (1989) 154–159). G-CSF activity is also associated with mobilization of hematopoietic stem cells from the marrow to the peripheral blood. (Haylock et al., *Blood* 89:2233–2258, 1997).

Despite the success of recombinant G-CSF in producing an agonist response at the G-CSF receptor, it is not considered an ideal pharmaceutical treatment. Lack of oral bioavailability and a limited serum half-life limit the desirability and efficacy of recombinant G-CSF as a pharmaceutical agent. Consequently, the need exists to provide improved ligands which have agonist properties towards the G-CSF receptor.

The human G-CSF receptor was first sequenced in 1990 (Fukunaga, R., Seto, Y., Mizushima, S., and Nagata, S. Three different mRNAs encoding human granulocyte colony-stimulating factor receptor *Proc. Natl. Acad. Sci. U.S.A.* 87(22):8702–8706, 1990) and had already been characterized by radioligand studies on purified human blood neutrophils by 1986 (Nicola N A; Vadas M A; Lopez A F, J-Cell-Physiol. 1986, 128 501-9). Notwithstanding the fact that assay tools have been available for over a decade, only one application (PCT/US97/08864) describes small organic molecules which exhibit G-CSF mimetic activity. This application does not mention zinc chelated small organic molecules.

As disclosed herein it has unexpectedly been discovered that certain selected zinc chelated receptor ligands have agonist properties towards the G-CSF receptor.

This discovery, that zinc chelated small organic molecules exhibit agonist activity towards the G-CSF receptor is particularly surprising in view of the finding that the natural ligand for the G-CSF receptor (i.e. G-CSF or recombinant G-CSF) does not utilize zinc chelation during activation. This finding is exemplified and further discussed in the examples below.

SUMMARY OF THE INVENTION

Accordingly, one aspect of the present invention is a method for agonizing the G-CSF receptor comprising contacting the receptor with a zinc chelated G-CSF receptor ligand.

Another aspect of the invention is a method for identifying agonists of the G-CSF receptor.

A third aspect of the invention relates to zinc chelated G-CSF receptor ligands.

A fourth aspect of the invention relates to an isolated G-CSF receptor binding moiety of a zinc chelated G-CSF receptor ligand.

A fifth aspect of the invention is a method for making zinc chelated G-CSF receptor ligands.

BRIEF DESCRIPTION OF THE DRAWINGS

FIG. 2 shows the same type of experiment in NFS60 cells, but run in the presence of 1 uM zinc (II). The activity of compound 1a is about 350% over control, which indicates that zinc(II) potentiates the activity of compound 1a.

DETAILED DESCRIPTION OF THE INVENTION

Figure 1:
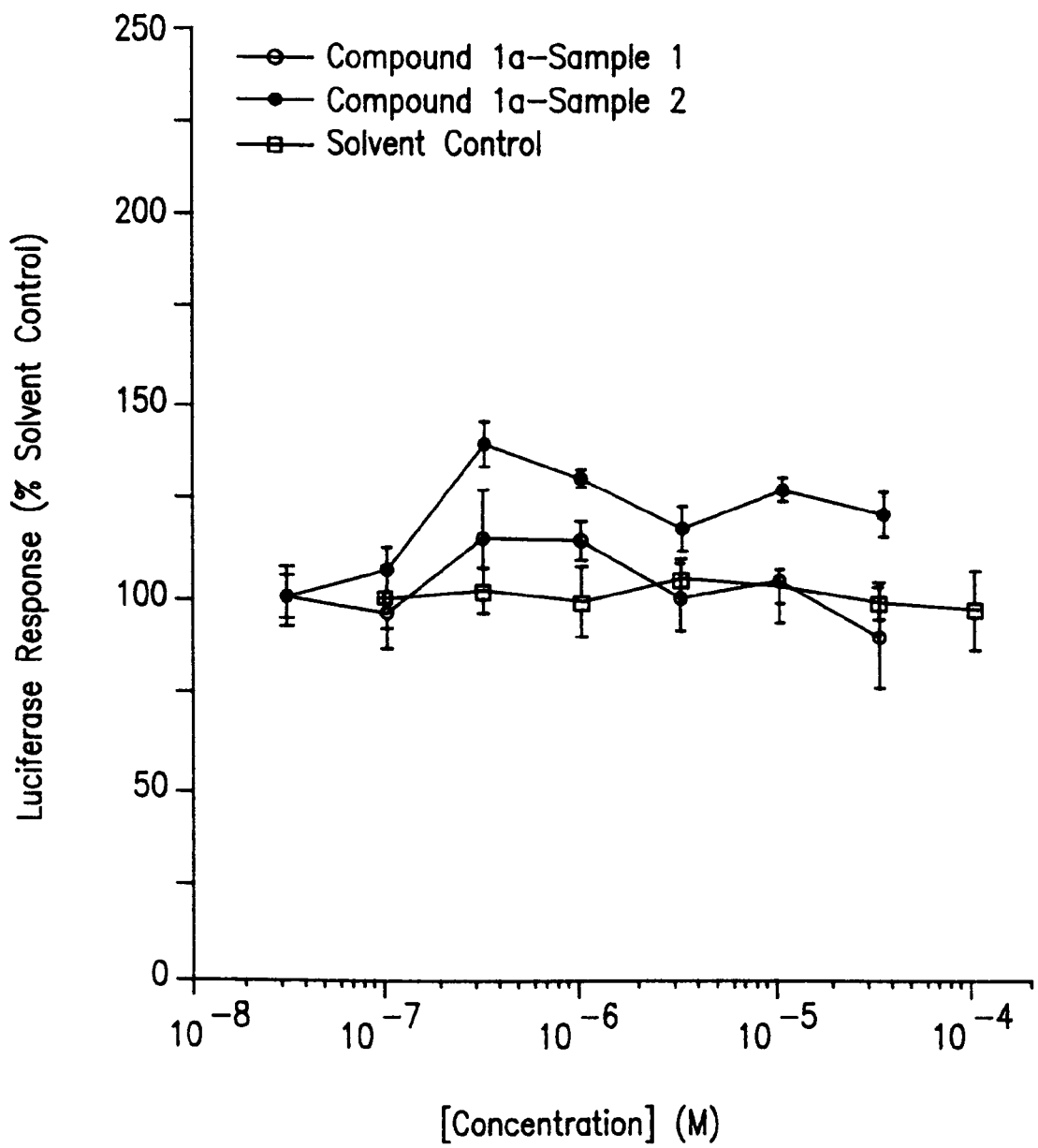
FIG. 1 shows the activity of two different samples of compound 1a (from Example 1) on the murine myeloid cell line NFS60 that contained a G-CSF-responsive element linked to a minimal promoter and the gene for luciferase. Activity of compound 1a is below the threshold of 150% over background. The study was performed as a Luciferase assay configured on the G-CSF-responsive NFS60 cell line as described in Tian et al., Science 281, 257–259 (1998). The experiments shown in FIGS. 2–8 used the same NFS60 cell line.

All publications, including but not limited to patents and patent applications, cited in this specification are herein incorporated by reference as though fully set forth.

By the term "heteroatom(s)", as used herein is meant nitrogen, oxygen or sulfur, preferably nitrogen.

By the term "treating" and derivatives thereof as used herein, is meant prophylatic or therapeutic therapy.

By the term "organic molecule" and derivatives thereof as used herein, is meant the standard usage in the art to the ordinary organic chemist and as such excludes inorganic molecules and peptide molecules.

By the phrase "mobilizing peripheral blood stem cells" as used herein is meant the mobilization of hematopoietic stem cells from the marrow to the peripheral blood.

The zinc chelated receptor ligands of this invention that have agonist properties towards the G-CSF receptor are compounds that consist of one or more G-CSF receptor binding moieties, preferably 1 to 4 moieties, most preferably 1 or 2 moieties, wherein each G-CSF receptor binding moiety forms at least two coordinate bonds to each of one or more zinc ions, preferably each moiety will form two or three coordinate bonds to each of one or two zinc ions.

By the term "G-CSF receptor binding moiety", and derivatives thereof, as used herein means a small organic molecule having a molecular weight from about 100 to about 850, preferably having a molecular weight from about 200 to about 750, most preferably having a molecular weight from about 300 to about 650 and having from 1 to 4 zinc binding motifs, preferably having one or two zinc binding motifs. In one embodiment, metal chelation forms a symmetrical multimer, such as a dimer, of the receptor binding moiety.

By the term "zinc binding motif", and derivatives thereof, as used herein means a continuation of atoms within a G-CSF receptor binding moiety that have the following characteristics:

1) each continuation consist of 3 to 10 atoms, preferably 4 to 8 atoms, most preferably 4 or 5 atoms,
2) each continuation further consisting of two or more heteroatoms, preferably from 2 to 4 heteroatoms, most preferably 2 to 3 heteroatoms, preferably at least one of the heteroatoms is nitrogen, wherein the heteroatoms are separated from each other by one to four additional atoms selected from the group consisting of carbon, nitrogen, sulfur and oxygen, preferably carbon or nitrogen, preferably by 2 to 4 additional atoms, most preferably by 2 or 3 additional atoms, and
3) the configuration of heteroatoms within the zinc binding motif allows for chelate coordination to a zinc (II) ion by providing for the formation of at least two coordinate bonds, preferably two or three coordinate bonds, simultaneously to a zinc ion.

Examples of zinc binding motifs for use in the present invention include but are not limited to the following:
—N—C—C—N—, —N—C=C=N—, —N—C—C=N—, —N=C—C—N—, —O—C—C—N—, —O—C=C—N—, —O—C—C=N—, —O=C—C=N—, —S—C—C—N—, —S—C=C—N—, —S—C—C=N—, —S=C—C=N—, —S—C—C—S—, —N=C—N—N—, —N—C—N—N—, —O=C—N—N—, —S=C—N—N—, —O—C—C=O—, —O—N—C=O—, —N=C—N—C=N—, —O=C—N—C=N—, —N=C—C=C=N—, —O—C=C—C=O—, —N—C—C—C—N—, —N—C—C=C—N—, —N=C—C=C—N—, —N=C—C=C—O—, —N=C—C=C—S—, —S=C—C=C—S—, —O=C—N—C=N—, —N—N—C—C=N—, —N—N—C—N—N—, —N—C=N—C=N—, —N=C—N—C=N—C—C—N— and —N=C—N—C=N—C—C=N—.

Preferred G-CSF receptor binding moieties of the present invention comprise one or more of the following functional groups, preferably one or two of the following functional groups: 2-guanidinobenzimidazoles, 2-guanidinobenzoxazoles, 2-guanidionbenzothiazole, 2-mercaptomethylpyridines, acylacetones, acylhydrazines, 2-aminoethanethiols, 2-(imidazol-4-yl)ethylamines, 2-(imidazol-2-yl)ethylamines, 2-(imidazol-4-yl)ethylimines, 2-(imidazol-2-yl)ethylimines, 2-picolylamine, 8-hydroxyquinolines, 8-aminoquinolines, 8-mercaptoquinolines, ethylenediamines, pyridine-2-carboxaldimines, 2,2'-bipyridyls, 2-thiobenzaldimines, 2-hydroxybenzaldimines and 2,5-diimino-3a,6a-diaryl-1,2,3,3a,4,5,6,6a-octahydroimidazo[4,5-d]imidazoles.

The above functional groups will generally form part of a larger molecule and may be further substituted in the formation of a G-CSF receptor binding moiety. Preferred substituents for optional use on the above functional groups consist of one or more groups selected from the following: alkyl, aryl, hydroxy, alkoxy, acyloxy, carbamoyl, amino, N-acylamino, ketone, halogen, cyano, thio, carboxy and carboxamido.

As noted from the depiction of bis{2,5-bis[2-benzimidazolylimino]-3a,6a-bis(2-pyridyl)-1,2,3,3a,4,5,6,6a-octahydroimidazo[4,5-d]imidazole-N,N'}-zinc(II) in Example 1 below, an 8 atom zinc binding motif (specifically the —N=C—N—C=N—C—C=N—) is essentially an overlap of a 5 atom zinc binding motif (that is —N=C—N—C=N—) and a 4 atom zinc binding motif (that is —N—C—C=N—) in a continuation. As such, preferred zinc binding motifs of the instant invention consist of a continuation of 4 or 5 atoms either individually or as part of a combination. Further, each atom of a zinc binding motif of the present invention may be further substituted, may be saturated or contain various degrees of unsaturation or may form part of a larger linear system or an aromatic or nonaromatic ring system.

The zinc chelated G-CSF receptor ligands of this invention are included in the pharmaceutical compositions of the invention and used in the methods of the invention. The G-CSF receptor binding moieties of this invention are included in the pharmaceutical compositions of the invention and used in the methods of the invention.

By the term "co-administering" and derivatives thereof as used herein is meant either simultaneous administration or any manner of separate sequential administration of a zinc chelated G-CSF receptor ligand, as described herein, and a further active ingredient or ingredients, such as antibacterial agents, antifungal agents as well as agents known to treat neutropenia, including chemotherapy-induced neutropenia and bone marrow transplantation and in mobilizing peripheral blood stem cells and other conditions with depressed leukocyte production. Preferably, if the administration is not simultaneous, the agents are administered in a close time proximity to each other. Furthermore, it does not matter if the agents are administered in the same dosage form, e.g. one agent may be administered subcutaneously and another agent may be administered orally.

The zinc chelated G-CSF receptor ligands of this invention are prepared by reacting one or more G-CSF receptor binding moieties and a zinc ion source, such as $Zn(NO_3)_2$, in a solvent, followed by optional isolation of the zinc chelated G-CSF receptor ligand. The order in which the indicated ingredients are utilized in the presently invented process is not critical. All orders of addition of the indicated ingredients are within the scope of the invention. Further, the zinc chelated G-CSF receptor ligands of this invention can be prepared in vivo by the administration of a G-CSF receptor binding moiety to a subject and utilization of naturally occurring zinc ions in the body of the subject.

Pharmaceutically acceptable salts, hydrates and solvates are formed when appropriate by methods well known to those of skill in the art.

Because the pharmaceutically active compounds of the present invention are active as agonist of the G-CSF receptor they exhibit therapeutic utility in treating bacterial infections, fungal infections, neutropenia, including chemotherapy-induced neutropenia and bone marrow transplantation and in mobilizing peripheral blood stem cells and other conditions with depressed leukocyte production.

In determining the potency of the presently invented compounds as agonist of the G-CSF receptor, the following assays are employed:

Luciferase Assay

Compounds of the present invention were tested for potency as agonist of the G-CSF receptor in a Luciferase reporter gene assay such as described in Tian et al., *Science* 281, 257–259 (1998). The NFS60 cells (Holmes, et al., *Proc. Natl. Acad. Sci.* USA 82:6687–6691 (1985)) were selected because they express endogenous G-CSF receptors closely matching the pattern of STAT (signal transducers and activators of transcription) activation observed in primary murine and human bone marrow cells.

Luciferase Assay and EDTA

In order to determine the requisiteness of zinc chelation of small organic molecules to agonist activity at the G-CSF receptor, the above luciferase assay was performed in the presence of EDTA. EDTA is a strong metal chelator and had as its only effect, the removal of zinc from the ligand-receptor interaction.

CFU-G Assay

Compounds of this invention are also tested for activity in the following assays: CFU-G assay (an example of which is described in King A. G., Talmadge J., Badger A. M., Pelus L. M. Regulation of colony stimulating activity production from bone marrow stromal cells by the hematoregulatory peptide, HP-5. *Exp. Hematol.* 20:223–228, 1992) and in vivo evaluation of peripheral blood neutrophil and monocyte count in the mouse (an example of which is described in Pelus, L. M.; King, A. G.; Broxmeyer, H. E.; DeMarsh, P. L.; Petteway, S. R.; Bhatnagar, P. K., *In vivo modulation of hematopoiesis by a novel hematoregulatory peptide* Exp-Hematol. 1994 22(3):239–47). In order to confirm the requirement for zinc(II) chelation, the above CFU-G assay was also conducted in the presence of EDTA.

Isothermal Titration Microcalorimetry

Zinc-mediated affinity of compounds from this invention for the G-CSF receptor was measured by isothermal titration microcalorimetry experiments. Titration microcalorimetry detects binding as heat originating from the intrinsic bond forming enthalpy change. In this assay, the compounds were titrated first against zinc(II) alone. In a separate experiment, the compounds were then assayed in the presence of zinc and a G-CSF/Fc fusion protein, which contained the extracellular domain of the G-CSF receptor presented in a dimeric form due to the Fc component. Interaction with G-CSF/Fc was confirmed from the binding enthalpy change, which was substantially increased over that of zinc alone. When the latter experiment was carried out in the absence of zinc, no heat of binding was detected, indicating that no interaction with G-CSF/Fc occurred under those conditions.

Compounds 1a and 3a bind to the G-CSF/Fc fusion protein with high, submicromolar affinity only in the presence of zinc. Compounds 1, 1a, 2a, and 3a showed activation above 150% of control between the concentration range of 1 to 100 micromolar in the luciferase assay. Further, compound 1a and 3a showed activation above 150% of control between the concentration range of 1 to 100 mnicromolar in the murine CFU-G assay. Compounds 1a and 3a showed elevation of peripheral blood neutrophil and monocyte count in the mouse.

Figure 2:
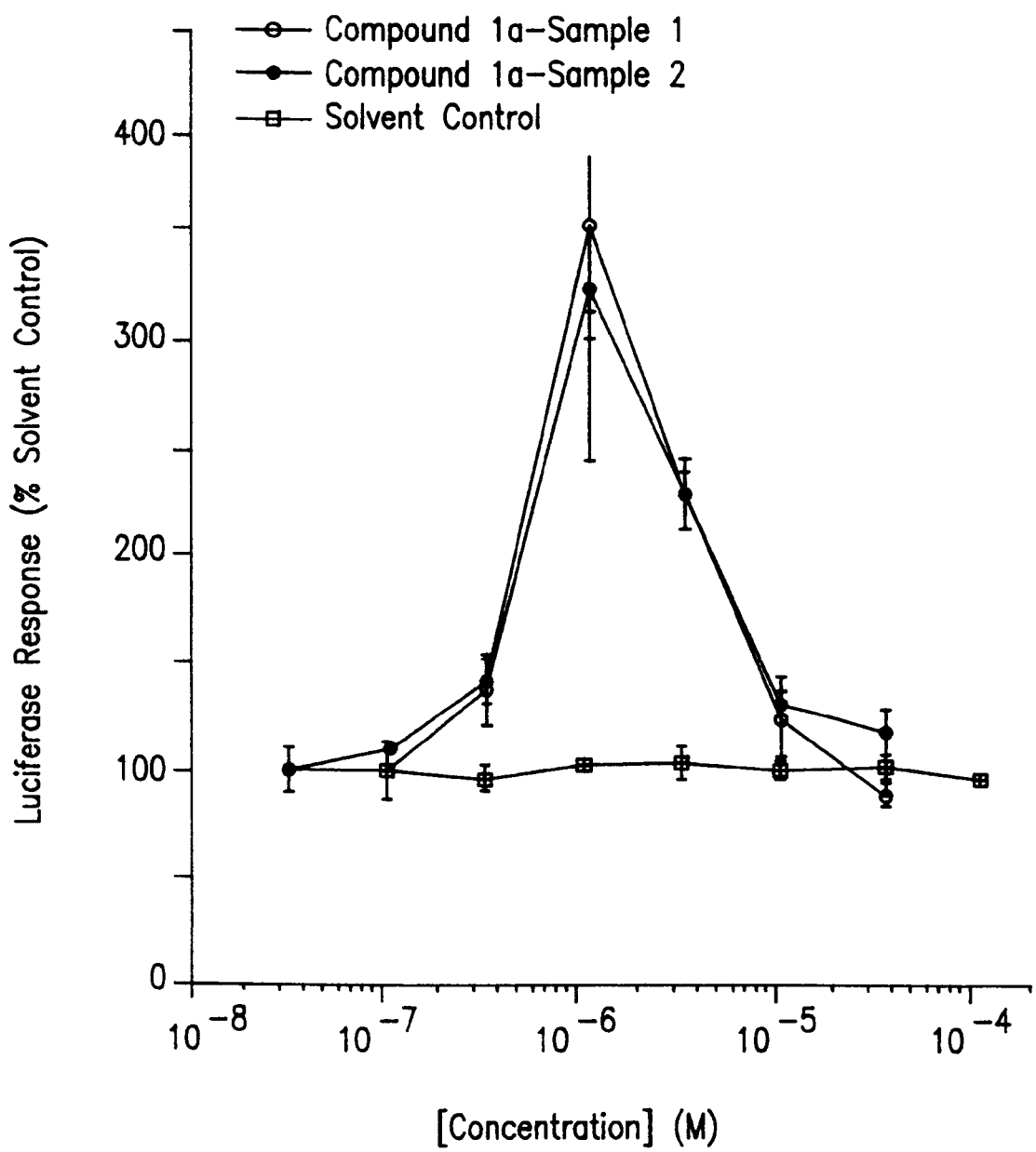

As demonstrated by the results depicted in FIG. 1, the G-CSF agonist activity of Compound 1a in the absence of zinc is below the activity threshold of 150% over background. However, as shown in FIG. 2, the presence of 1 uM zinc(II) activates compound 1a, so that it becomes a G-CSF agonist with an efficacy of 350% over background at 1 uM. This is an indication that zinc(II) mediates the activity of compound 1a.

Figure 3:
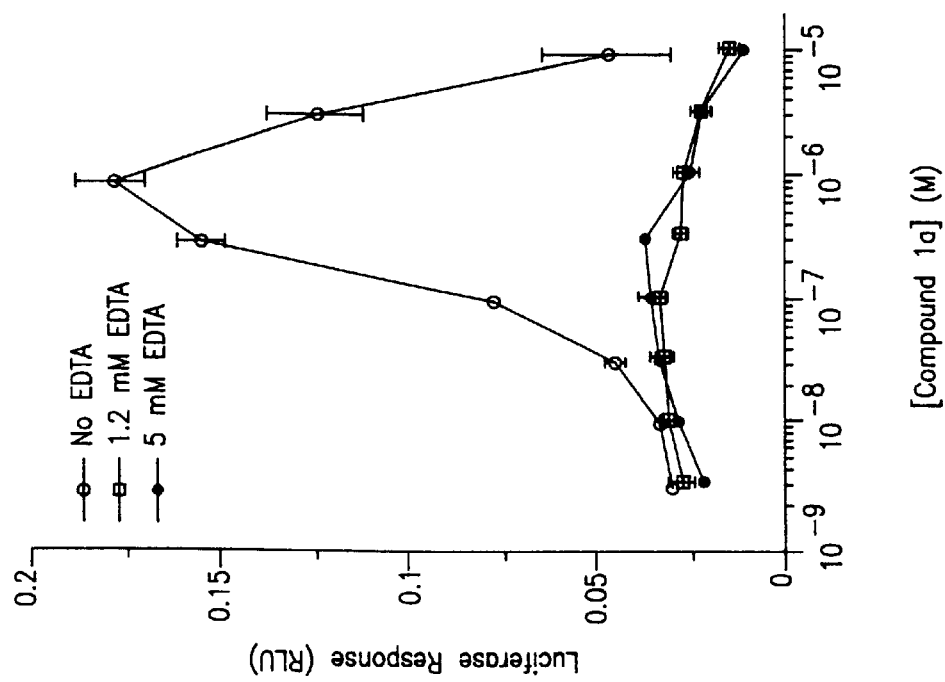
FIG. 3 is an analysis of the effect of ethylenediaminetetraacetic acid (as used herein—EDTA) on the activity of Compound 1a (from Example 1) in NFS60 cells. Shown are luciferase response curves of Compound 1a at the indicated concentrations and in the presence of various concentrations of EDTA. EDTA at 1.2 millimolar concentration antagonized the activity of compound 1a. The media in this assay contained a small amount (1–5 uM) of zinc(II).

As demonstrated by the results depicted in FIG. 3, the G-CSF agonist activity of Compound 1a was abrogated in the presence of EDTA, confirming that a metal ion mediates the activity.

Figure 4:
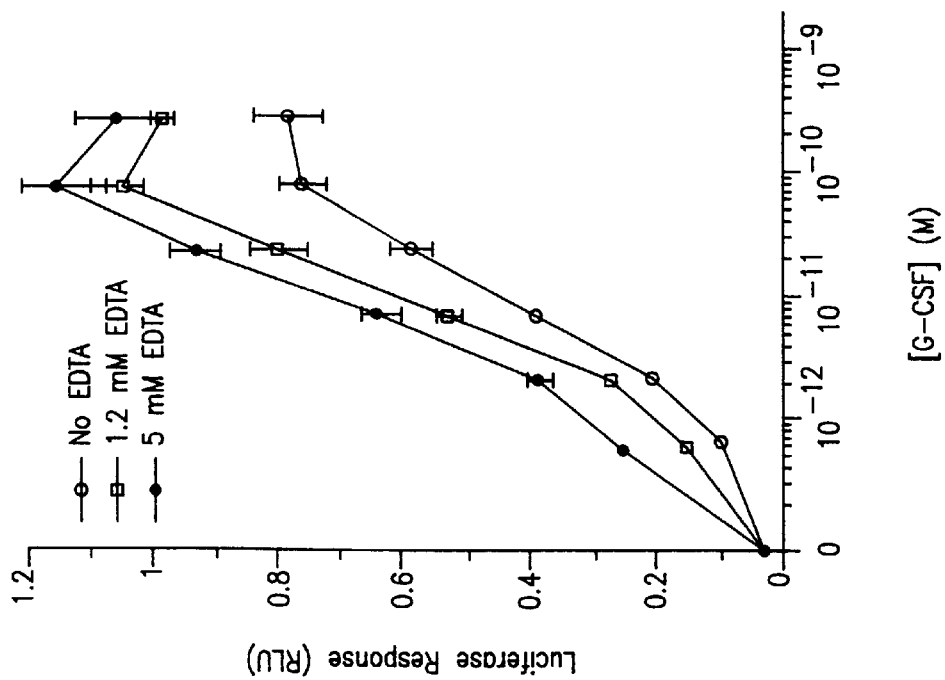
FIG. 4 is an analysis of the effect of EDTA on the activity of recombinant G-CSF on NFS60 cells. Shown are luciferase response curves of recombinant G-CSF at the indicated concentrations and in the presents of various concentrations of EDTA. EDTA at both 1.2 and 5 millimolar has little effect on the activity of recombinant G-CSF in the assay.

Conversely, the results depicted in FIG. 4 indicate that the agonist activity of the natural ligand (i.e. G-CSF or recombinant G-CSF as used herein) is not mediated by metal ions.

Figure 6:
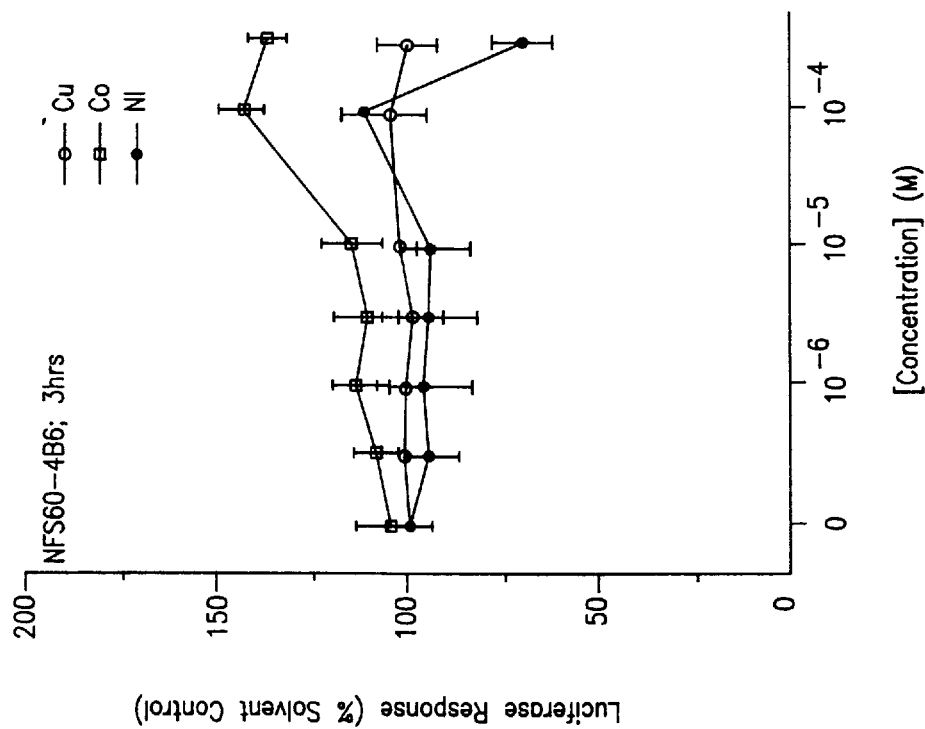
FIGS. 5 and 6 depict an analysis of the activity of metal chlorides alone on the basal luciferase level of NFS60 cells. Shown are luciferase response curves of the indicated metal chlorides at various concentrations. None of the metals have a meaningful effect on the basal luciferase levels at concentrations equal or less than 10 micromolar.
Figure 5:
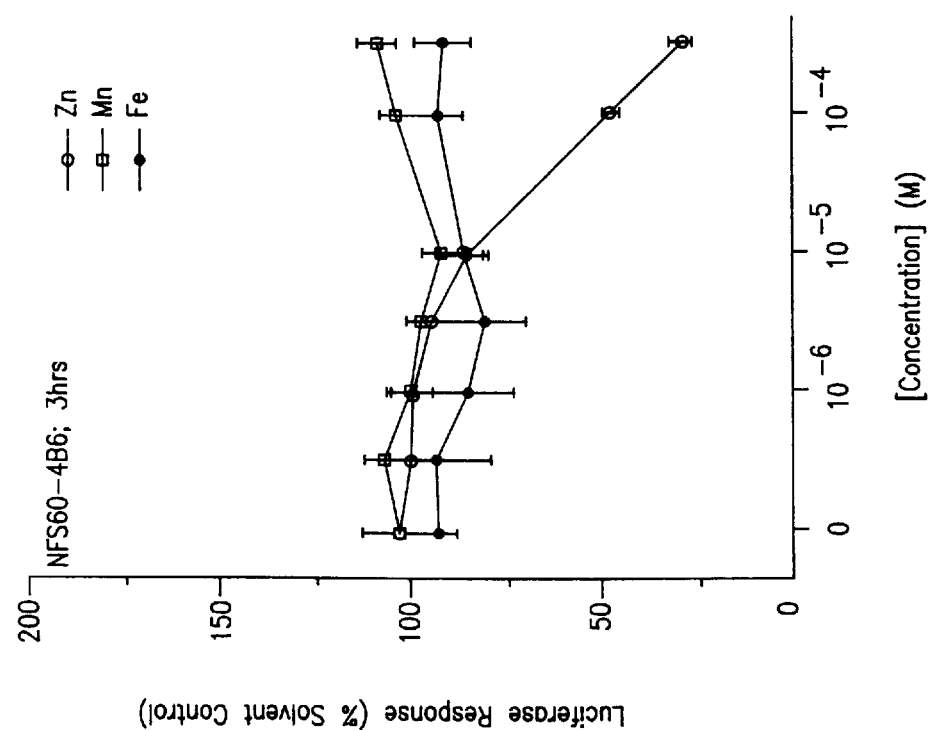

The results depicted in FIGS. 5 and 6 indicate that metal ions alone are insufficient to trigger an agonist response at the G-CSF receptor.

Figure 8:
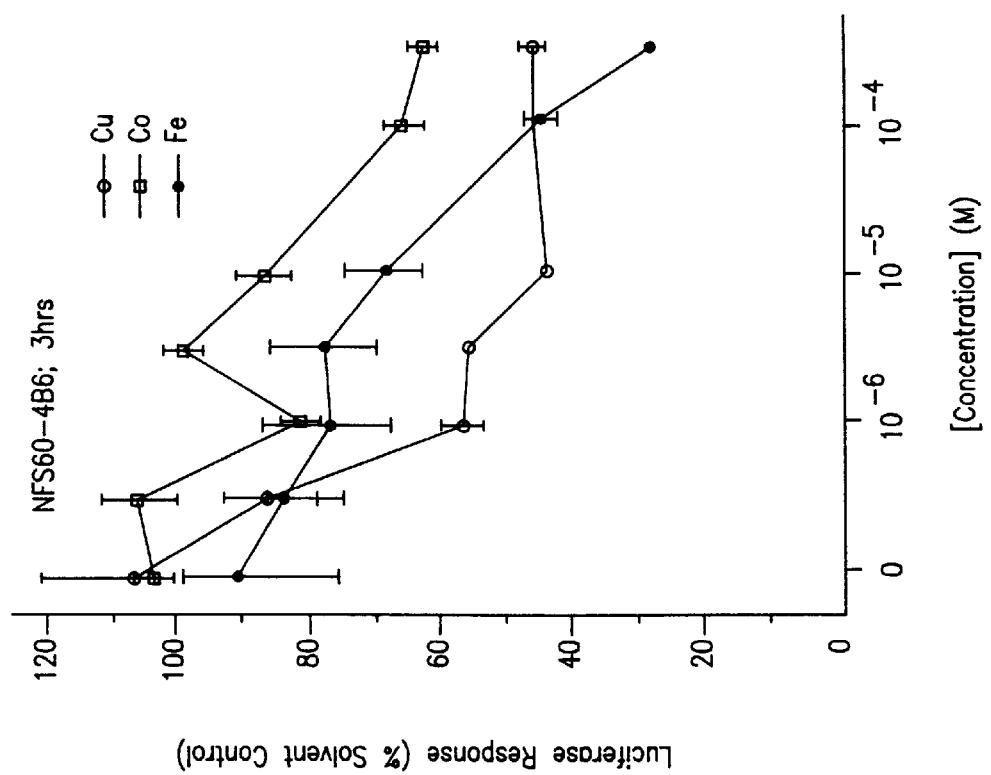
FIGS. 7 and 8 show an analysis of the effect of metal chlorides on the EDTA depleted activity of Compound 1a on NFS60 cells. Shown are luciferase response curves as effected by the indicated metal chlorides. Only zinc (II) at concentrations 0.5–10 micromolar can overcome the inhibition in luciferase activity caused by 50 micromolar concentration of the metal chelator EDTA. None of the other metals tested could overcome the inhibitory effect of EDTA.
Figure 7:
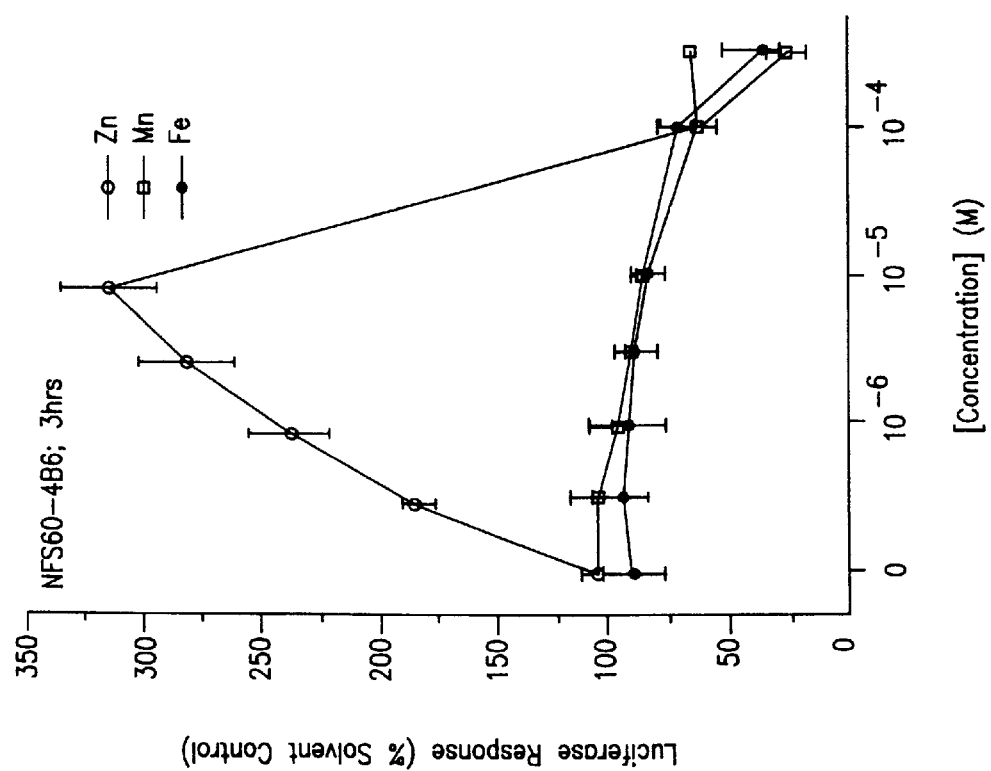

The results depicted in FIGS. 7 and 8 indicate that chelation of a small molecule to zinc ions (and not ions of manganese, iron, copper or cobalt) is a requirement for activation of the G-CSF receptor by organic molecules.

The results depicted in FIGS. 1 through 8 demonstrate, for the first time, that zinc chelated small molecules, or zinc chelated receptor ligands as used herein, are necessary for activation of the G-CSF receptor by organic molecules.

Based on the description in the specification and in the Examples one of skill in the art can readily design and prepare a zinc chelated G-CSF receptor ligand. Further, one of skill in the art can readily determine if a G-CSF receptor ligand candidate is acting as an agonist of the G-CSF receptor by using the assays described herein and then repeating the experiments of FIGS. 1 through 8.

The pharmaceutically active compounds within the scope of this invention are useful as G-CSF mimetics in mammals, including humans, in need thereof.

The present invention therefor provides a method of treating bacterial infections, fungal infections, neutropenia, including chemotherapy-induced neutropenia and bone marrow transplantation and in mobilizing peripheral blood stem cells and other conditions with depressed leukocyte production, which comprises administering a zinc chelated G-CSF receptor ligand in a quantity effective to enhance leukocyte production. The zinc chelated G-CSF receptor ligands of the present invention also provide for a method of treating the above indicated disease states because of their demonstrated ability to act as agonist of the G-CSF receptor. The drug may be administered to a patient in need thereof by any conventional route of administration, including, but not limited to, intravenous, intramuscular, oral, subcutaneous, intradermal, and parenteral. Also, the drug may be formed in vivo by the administration of a G-CSF receptor binding moiety by the same methods of administration described herein and in about the same amounts as described herein for zinc chelated G-CSF receptor ligands. Further, the possibility exists that solubility and bioavailability concerns will be associated with the zinc chelated G-CSF receptor ligands of the present invention. Thus, depending on the particular moiety in question, it will often be preferable to administer a G-CSF receptor binding moiety of the present invention and therein by subsequently form a zinc chelated G-CSF receptor ligand in vivo using plasma as the solvent and naturally occurring zinc ions. It is also contemplated herein that a receptor binding moiety of the present invention be administered with a zinc source so as to facilitate the in vivo formation of a zinc chelated G-CSF receptor ligand.

The pharmaceutically active zinc chelated G-CSF receptor ligands of the present invention or, when desired and appropriate, the G-CSF receptor binding moieties of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active zinc chelated G-CSF receptor ligands of the present invention or, when desired and appropriate, the G-CSF receptor binding moieties of the present invention, in a pharmaceutical dosage unit as described above will be an efficacious, nontoxic quantity preferably selected from the range of 0.001–125 mg/kg of active compound, preferably 0.001–60 mg/kg. When treating a human patient in need of an agonist of the G-CSF receptor, the selected dose is administered preferably from 1–6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular zinc chelated G-CSF receptor ligand or G-CSF receptor binding moiety in use, the strength of the preparation, the mode of administration, and the advancement of the disease condition. Additional factors depending on the particular patient being treated will result in a need to adjust dosages, including patient age, weight, diet, and time of administration.

Another aspect of the present invention is a method for identifying agonists of the G-CSF receptor and G-CSF receptor ligands identified thereby. In the method, the G-CSF receptor is contacted with G-CSF receptor ligand candidates in the presence of a micromolar concentration of zinc(II). Ligand candidates which bind to the G-CSF receptor are selected by receptor binding assays well known to those skilled in the art, such as competitive and non-competitive binding measurements (*Immobilized Affinity Ligand Techniques,* G. T. Hermanson, A. K. Mallia, P. K. Smith Eds., Academic Press Inc. San Diego, Calif. 1992), isothermal microcalorimetry (*Rapid Measurement of Binding Constants and Heats of Binding Using a New Titration Calorimeter* T. Wiseman, S. Williston, J. F. Brandts, and L.-N. Lin (1989) *Analytical Biochemistry* 179, 131–137.), sedimentation equilibrium (T. Horan et al. *Biochemistry* 1996, 35, 4886–4896), ELISA, RIA methodologies (*An Introduction to Radioimmunoassays and Related Techniques,* T. Chard, Elsevier Science Publishers, Amsterdam, The Netherlands, 1990), BIAcore® (*BIAtechnology Handbook,* Pharmacia Biosensor AB, Uppsala, Sweden, 1994), fluorescence anysotropy methodology (*Luminesct Spectroscopy of Proteins,* E. A. Permyakov, CRC Press Inc., Boca Raton, Fla. 1992), flow cytometry technology (*Flow Cytometry and Cell Sorting,* A. Radbruch, Springer-Verlag, New York, N.Y. 1992).

In general, the G-CSF receptor in isolated, immobilized or cell-bound form is contacted with a plurality of zinc chelated G-CSF receptor ligand candidates and those candidates which bind to and interact with the receptor are selected. Optionally, the isolated, immobilized or cell-bound G-CSF receptor is contacted with a variety of metal-chelating G-CSF receptor ligand candidates in the presence of zinc(II). Binding interaction can be measured directly by using radioactively labeled ligand candidates or indirectly, by using cells expressing the G-CSF receptor and measuring the occurrence of an event mediated by the formation of a G-CSF receptor—ligand complex. Alternatively, the ligand candidates can be subjected to competitive binding assays in which the known receptor ligand, labeled preferably with an analytically detectable reagent, most preferably radioactivity, is included with the ligand candidates and a candidate's ability to inhibit the binding of the labeled ligand is measured.

Positive G-CSF receptor ligand candidates are screened for biological function by any one of the G-CSF receptor function assays well known to those skilled in the art. It is expected that a positive ligand binding candidate will exhibit agonist activity in receptor function assays.

An example of an appropriate competitive binding assay involves the immobilization of the G-CSF receptor and incubation with compounds of interest with $I^{125}$ radiolabeled G-CSF following the general procedure already described for other cytokine receptors (C. L. Martens et al. J. Biol. Chem. 1995, 270, 21129, E. Whitehorn et al. Biotechnology 1995, 13, 1215, S. D. Yanofsky et al. Proc. Natl. Acad. Sci. U.S.A. 1996, 93, 7381, N. C. Wrighton et al. Science, 1996, 273, 458, S. E. Cwirla, Science, 1997, 276, 1696).

The method of this invention of inducing agonist activity at the G-CSF receptor in mammals, including humans, comprises administering to a subject in need of such activity an effective amount of a pharmaceutically active zinc chelated G-CSF receptor ligand of the present invention or, when desired and appropriate, a G-CSF receptor binding moiety of the present invention.

The invention also provides for the use of a presently invented zinc chelated G-CSF receptor ligand or a presently invented G-CSF receptor binding moiety in the manufacture of a medicament for use as an agonist of the G-CSF receptor.

The invention also provides for the use of a zinc chelated G-CSF receptor ligand or a G-CSF receptor binding moiety in the manufacture of a medicament for use in therapy.

The invention also provides for the use of a zinc chelated G-CSF receptor ligand or a G-CSF receptor binding moiety in the manufacture of a medicament for use in enhancing leukocyte production.

The invention also provides for the use of a zinc chelated G-CSF receptor ligand or a G-CSF receptor binding moiety in the manufacture of a medicament for use in treating bacterial and fungal infections.

The invention also provides for a pharmaceutical composition for use as an agonist of the G-CSF receptor which comprises a zinc chelated G-CSF receptor ligand or a G-CSF receptor binding moiety and a pharmaceutically acceptable carrier.

The invention also provides for a pharmaceutical composition for use in the treatment of neutropenia which comprises a zinc chelated G-CSF receptor ligand or a G-CSF receptor binding moiety and a pharmaceutically acceptable carrier.

The invention also provides for a pharmaceutical composition for use in enhancing leukocyte production which comprises a zinc chelated G-CSF receptor ligand or a G-CSF receptor binding moiety and a pharmaceutically acceptable carrier.

The invention also provides for a pharmaceutical composition for use in treating bacterial infections which comprises a zinc chelated G-CSF receptor ligand or a G-CSF receptor binding moiety and a pharmaceutically acceptable carrier.

The invention also provides for a pharmaceutical composition for use in treating fungal infections which comprises a zinc chelated G-CSF receptor ligand or a G-CSF receptor binding moiety and a pharmaceutically acceptable carrier.

The invention also provides for a process for preparing a pharmaceutical composition containing a pharmaceutically acceptable carrier or diluent and a zinc chelated G-CSF receptor ligand or a G-CSF receptor binding moiety which comprises bringing the zinc chelated G-CSF receptor ligand or the G-CSF receptor binding moiety into association with the pharmaceutically acceptable carrier or diluent.

No unacceptable toxicological effects are expected when compounds of the invention are administered in accordance with the present invention.

In addition, the pharmaceutically active compounds of the present invention can be co-administered with further active ingredients, such as other compounds known to treat bacterial infections, fungal infections, neutropenia, including chemotherapy-induced neutropenia and bone marrow transplantation and in mobilizing peripheral blood stem cells and other conditions with depressed leukocyte production, or compounds known to have utility when used in combination with an agonist of the G-CSF receptor.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL DETAILS

EXAMPLE 1

Preparation of Compound 1

Bis{2,5-bis[2-benzimidazolylimino]-3a,6a-bis(2-pyridyl)-1,2,3,3a,4,5,6,6a-octahydroimidazo[4,5-d]imidazole-N,N'}-zinc(II)

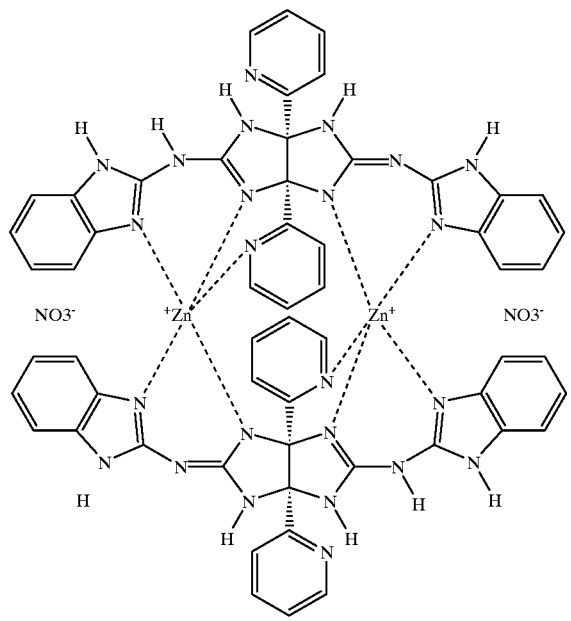

a) Preparation of Compound 1a 2,5-Bis[2-benzimidazolylimino]-3a,6a-bis(2-pyridyl)-1,2,3,3a,4,5,6,6a-octahydroimidazo[4,5-d]imidazole.

A mixture of 2,2'-pyridil (15.8 g, 74.4 mmol) and 2-guanidinobenzimidazole (19.5 g, 111.7 mmol) in methanol (440 mL) was treated with a solution of sodium hydroxide (2.97 g, 74.4 mmol) in 74 mL and the resulting mixture was left standing at room temperature for 4 days. The crystalline material was filtered and dried under vacuum to yield 21.1 g of the title compound as off-white crystals (72%). mp: 305–307° C. (dec); HPLC retention time 4.5 min (reversed phase, Beckman ultrasphere ODS 4.6 mm×25 cm column, 20 min gradient elution with 20:80 to 60:40 acetonitrile:water containing 0.1% TFA@2 mL/min); $^1$H NMR (300 MHz, $d_6$-DMSO) d 11.5 (br s, NH, 2 H), 10.0 (br s, NH, 2 H), 8.6 (br s, NH, 2 H), 8.38 (d, J=4.2 Hz, 2 H), 7.55 (t, J=7.8 Hz, 2 H), 7.29 (d, J=7.8 Hz, 2 H), 7.27–7.21 (m, 4 H), 7.14 (br s, 2 H), 6.98 (dd, J=5.8, 3.2 Hz, 4 H); MS (ESI) m/z 527 [M+H]$^+$; Anal. Calcd. for $C_{28}H_{22}N_{12}$. $^2/_3H_2O$: C, 62.44; H, 4.37, N, 31.21; Found: C, 62.72; H, 4.08; N, 30.86.

b) Preparation of Compound 1

Bis{2,5-bis[2-benzimidazolylimino]-3a,6a-bis(2-pyridyl)-1,2,3,3a,4,5,6,6a-octahydroimidazo[4,5-d]imidazole-N,N'}-zinc(II)

A solution of compound from Example 1a (40 mg, 0.076 mmol) in 2 mL of 10% aqueous acetic acid was treated with a solution of zinc nitrate hexahydrate (24.9 mg, 0.0836 mmol) in water (1 mL). The mixture was left standing at room temperature for 6 h, and was then centrifuged, decanted and rinsed with water three times. The title compound was obtained as a white powder (13 mg). HPLC retention time 10.4 min (reversed phase, Beckman ultrasphere ODS 4.6 mm×25 cm column, 20 min gradient elution with 20:80 to 60:40 acetonitrile:water containing 0.1% TFA@2 mL/min); MS (ESI) m/z 1182 [M]$^+$, 591 [M]$^{++}$.

EXAMPLE 2

Preparation of Compound 2

Bis{2,5-bis[2-benzimidazolylimino]-3a,6a-diphenyl-1,2,3,3a,4,5,6,6a-octahydroimidazo[4,5-d]imidazole-N,N'}-zinc(II)

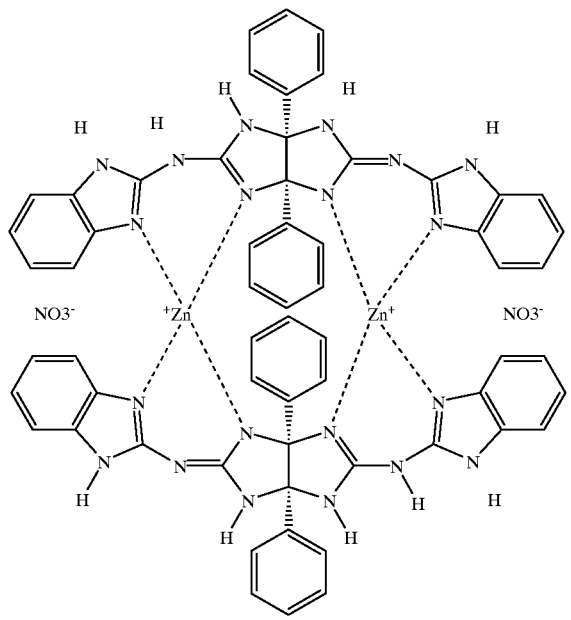

a) Preparation of Compound 2a 2,5-Bis[2-benzimidazolylimino]-3a,6a-diphenyl-1,2,3,3a,4,5,6,6a-octahydroimidazo[4,5-d]imidazole A mixture of benzil (1.05 g, 5.0 mmol) and 2-guanidinobenzimidazole (1.57 g, 9.0 mmol) in benzene (25 mL) was refluxed in pyridine (10 mL) for 1 h. After evaporating most of the pyridine under reduced pressure, the residue was treated with hot toluene and the resulting precipitate was filtered. The precipitate was then dissolved in 9:1 water:acetic acid (30 mL); the solution was filtered and the filtrate was neutralized to pH 7 with phosphate buffer. A precipitate formed, that was then collected and triturated with water to afford the title compound (0.42 g, 16%). $^1$H NMR (300 MHz, $d_6$-DMSO) d 11.5 (br s, NH, 2 H), 10.0 (br s, NH, 2 H), 8.6 (br s, NH, 2 H), 7.28–7.10 (m, 14 H), 6.97 (dd, J=6.0, 3.0 Hz, 4 H); MS (ESI) m/z 525 [M+H]$^+$; Anal. Calcd. for $C_{30}H_{24}N_{10}$ . $^1/_2CH_3CO_2H$ $^3/_4H_2O$: C, 65.37; H, 4.88; N, 24.65. Found: C, 65.36; H, 4.79; N, 24.48.

b) Preparation of Compound 2

Bis{2,5-bis[2-benzimidazolylimino]-3a,6a-diphenyl-1,2,3,3a,4,5,6,6a-octahydroimidazo[4,5-d]imidazole-N,N'}-zinc(II)

A solution of compound from Example 2a (50 mg, 0.095 mmol) in 2 mL of methanol containing a drop of formic acid was treated with a solution of zinc nitrate hexahydrate (31.0 mg, 0.104 mmol) in methanol (1 mL). The mixture was left standing at room temperature for 18 h, and was then centrifuged, decanted and rinsed with water three times to yield the title compound as a white powder (35 mg). MS (ESI) m/z 1178 [M]$^+$, 589 [M]$^{++}$.

EXAMPLE 3

Preparation of Compound 3

Bis{5-(2-benzimidazolylimino)-2-[(5-methyl-2-benzimidazolyl)imino]-3a,6a-bis(2-pyridyl)-1,2,3,3a,4,5,6,6a-octahydroimidazo[4,5-d]imidazole-N,N'}-zinc(II)

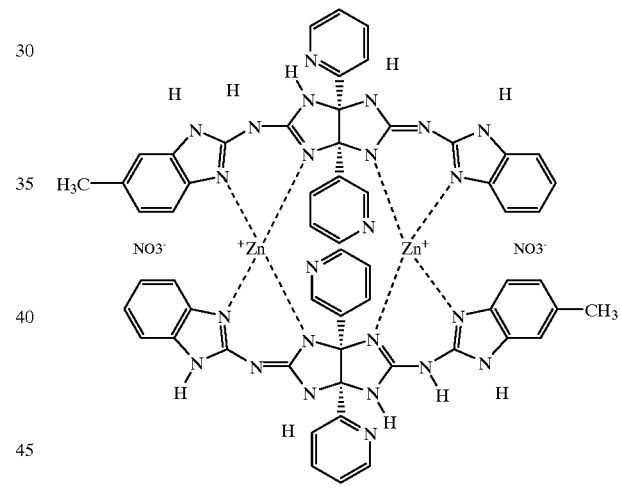

a) Preparation of Compound

3a -5-(2-benzimidazolylimino)-2-[(5-methyl-2-benzimidazolyl)imino]-3a,6a-bis(2-pyridyl)-1,2,3,3a,4,5,6,6a-octahydroimidazo[4,5-d]imidazole bis(trifluoroacetate) salt A mixture of 2,2'-pyridil (135 mg, 0.636 mmol), 2-guanidinobenzimidazole (92.8 mg, 0.530 mmol) and 5-methyl-2-guanidinobenzimidazole (100 mg, 0.530 mmol) in methanol (3 mL) was treated with a solution of sodium hydroxide (38 mg, 0.95 mmol) in 0.5 mL of water and the resulting mixture was left standing at room temperature for 2 days. The crystalline material was filtered and purified by reversed phase preparative HPLC (Rainin Dynamax, 5 µM C18 column: 21.4 mm×25 cm, elution with gradient acetonitrile-water containing 0.1% trifluoroacetic acid) to yield the title compound as a white powder (88 mg, 18%). $^1$H NMR (300 MHz, $d_6$-DMSO) δ13.0 (br s, NH, 4 H), 9.8 (br s, NH, 4 H), 8.39 (d, J=4.3 Hz, 2 H), 7.64 (td, J=7.8, 1.7 Hz, 2 H), 7.57 (d, J=7.8 Hz, 2 H), 7.49–7.46 (m, 2 H), 7.38–7.33 (m, 3 H), 7.27 (s, 1 H), 7.21–7.13 (m, 3 H), 2.44 (s, 3 H); MS (ESI) m/z 541 [M+H]+ b) Preparation of Compound 3

Bis{5-(2-benzimidazolylimino)-2-[(5-methyl-2-benzimidazolyl)imino]-3a,6a-bis(2-pyridyl)-1,2,3,3a,4,5,6,6a-octahydroimidazo[4,5-d]imidazole-N,N'}-zinc(II)

A solution of compound from Example 3a (70 mg, 0.091 mmol) in 10 mL of water was treated with a solution of zinc nitrate hexahydrate (40 mg, 0.136 mmol) in water (1 mL). The mixture was left standing at room temperature for 1 d, and was then centrifuged, decanted and rinsed with water three times. The title compound was obtained as a white powder (29 mg). HPLC retention time 11.8 min (reversed phase, Beckman ultrasphere ODS 4.6 mm×25 cm column, 20 min gradient elution with 20:80 to 60:40 acetonitrile:water containing 0.1% TFA@2 mL/min); MS (ESI) m/z 1210 [M]+, 605 [M]++.

EXAMPLE 4

Preparation of Compound 4

Bis{2,5-bis[(5-methyl-2-benzimidazolyl)imino]-3a,6a-bis(2-pyridyl)-1,2,3,3a,4,5,6,6a-octahydroimidazo[4,5-d]imidazole-N,N'}-zinc(II)

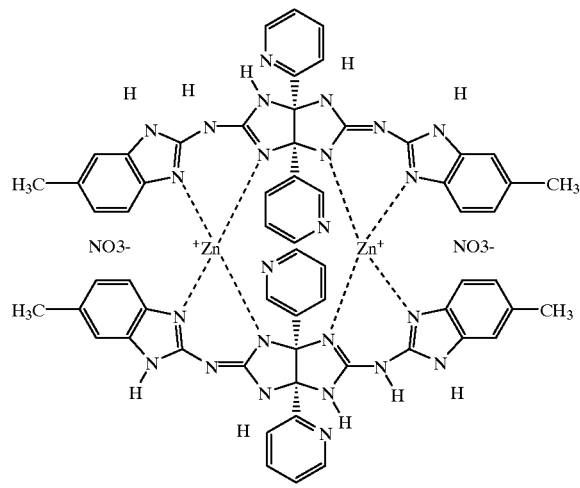

a) Preparation of Compound 4a 2,5-bis[(5-methyl-2-benzimidazolyl)imino]-3a,6a-bis(2-pyridyl)-1,2,3,3a,4,5,6,6a-octahydroimidazo[4,5-d]imidazole.

A mixture of 2,2'-pyridil (603 mg, 2.84 mmol) and 5-methyl-2-guanidinobenzimidazole (489 mg, 2.58 mmol) in methanol (17 mL) was treated with a solution of sodium hydroxide (113.6 mg, 2.84 mmol) in 2.8 mL of water. The title compound was isolated as a grey powder (450 mg, 63% yield). mp: 290–291° C. (dec); HPLC retention time 7.1 min (reversed phase, Beckman ultrasphere ODS 4.6 mm×25 cm column, 20 min gradient elution with 20:80 to 60:40 acetonitrile:water containing 0.1% TFA@2 mL/min); $^1$H NMR (300 MHz, d$_6$-DMSO) δ11.3 (br s, NH, 2 H), 10.0 (br s, NH, 2 H), 8.5 (br s, NH, 2 H), 8.32 (d, J=4.2 Hz, 2 H), 7.54 (t, J=7.6 Hz, 2 H), 7.31 (d, J=7.6 Hz, 2 H), 7.16 (d, J=7.8 Hz, 2 H), 7.16–7.09 (m, 2 H), 7.09 (s, 2 H), 7.14 (br s, 2 H), 6.86 (d, J=7.8, Hz, 2 H), 2.34 (s, 6 H); MS (ESI) m/z 555 [M+H]+.

b) Preparation of Compound 4

Bis{2,5-bis[(5-methyl-2-benzimidazolyl)imino]-3a,6a-bis(2-pyridyl)-1,2,3,3a,4,5,6,6a-octahydroimidazo[4,5-d]imidazole-N,N'}-zinc(II)

A solution of compound from Example 4a (50 mg, 0.091 mmol) in 10 mL of water containing a few drops of formic acid was treated with a solution of zinc nitrate hexahydrate (40 mg, 0.136 mmol) in water (1 mL). The mixture was left standing at room temperature for 1 d, and was then centrifuged, decanted and rinsed with water three times. The title compound was obtained as a white powder (19 mg). HPLC retention time 13.3 min (reversed phase, Beckman ultrasphere ODS 4.6 mm×25 cm column, 20 min gradient elution with 20:80 to 60:40 acetonitrile:water containing 0.1% TFA@2 ml/min); MS (ESI) m/z 1238 [M]+, 619 [M]++.

EXAMPLE 5

Capsule Composition

An oral dosage form for administering a presently invented agonist of the G-CSF receptor is produced by filing a standard two piece hard gelatin capsule with the ingredients in the proportions shown in Table I, below.

TABLE I

| INGREDIENTS | AMOUNTS |
| --- | --- |
| Bis{2,5-bis[2-benzimidazolylimino]-3a,6a-bis(2-pyridyl)-1,2,3,3a,4,5,6,6a-octahydroimidazo[4,5-d]-imidazole-N,N'}-zinc(II) (Compound 1) | 25 mg |
| Lactose | 55 mg |
| Talc | 16 mg |
| Magnesium Stearate | 4 mg |

EXAMPLE 6

Injectable Parenteral Composition

An injectable form for administering a presently invented agonist of the G-CSF receptor is produced by stirring 1.5% by weight of 2,5-Bis[2-benzimidazolylimino]-3a,6a-diphenyl-1,2,3,3a,4,5,6,6a-octahydroimidazo[4,5-d]imidazole (Compound 2a) in 10% by volume propylene glycol in water.

EXAMPLE 7

Tablet Composition

The sucrose, calcium sulfate dihydrate and a presently invented agonist of the G-CSF receptor, as shown in Table II below, are mixed and granulated in the proportions shown with a 10% gelatin solution. The wet granules are screened, dried, mixed with the starch, talc and stearic acid, screened and compressed into a tablet.

TABLE II

| INGREDIENTS | AMOUNTS |
| --- | --- |
| 2,5-Bis[2-benzimidazolylimino]-3a,6a-bis(2-pyridyl)-1,2,3,3a,4,5,6,6a-octahydroimidazo[4,5-d]imidazole (Compound 1a) | 20 mg |
| calcium sulfate dihydrate | 30 mg |
| sucrose | 4 mg |
| starch | 2 mg |
| talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A method for agonizing the G-CSF receptor in a subject in need thereof which comprises administering to the subject a therapeutically effective amount of a G-CSF receptor binding moiety;

except compounds of the formula:

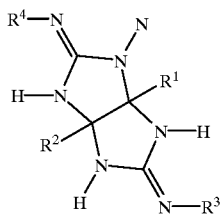

wherein $R^1$, $R^2$, $R^3$ and $R^4$ are independently aryl, where aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: C(O)NR$^6$R$^7$ and NR$^6$R$^7$, aryloxy, cycloalkyl, substituted cycloalkyl, akyl, $C_6$–$C_{12}$aryl, alkoxy, acyloxy, substituted $C_6$–$C_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy, acyloxy, $C_6$–$C_2$aryl, substituted $C_6$–$C_{12}$aryl, amino, N-acylano, oxo, hydroxy, cycloalkyl, substituted cycloalkyl, —C(O)OR$^6$, —S(O)$_n$R$^7$, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, $C_6$–$C_{12}$aryl substituted cycloalkyl, substituted $C_6$–$C_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; or a pharmaceutically acceptable salt, hydrate, solvate or ester thereof.

2. A method of enhancing leukocyte production in a subject which comprises administering to the subject a therapeutically effective amount of a compound of claim 1.

3. A method of treating neutropenia in a subject which comprises administering to the subject a therapeutically effective amount of a compound of claim 1.

4. The method of claim 1 wherein the G-CSF receptor is the human G-CSF receptor.

5. The method of claim 2 wherein the subject is a human.

6. The method of claim 3 wherein the subject is a human.

* * * * *